United States Patent
Nimura et al.

(10) Patent No.: US 11,446,418 B2
(45) Date of Patent: Sep. 20, 2022

(54) DIALYSATE SOLUTION CONTAINER

(71) Applicant: Nikkiso Co., Ltd., Tokyo (JP)

(72) Inventors: Hiroshi Nimura, Makinohara (JP);
Masato Fujiwara, Makinohara (JP);
Takayoshi Yokoyama, Makinohara (JP)

(73) Assignee: Nikkiso Co., Ltd., Tokyo (JP)

( * ) Notice: Subject to any disclaimer, the term of this patent is extended or adjusted under 35 U.S.C. 154(b) by 63 days.

(21) Appl. No.: 16/957,193

(22) PCT Filed: Dec. 11, 2018

(86) PCT No.: PCT/JP2018/045549
§ 371 (c)(1),
(2) Date: Jun. 23, 2020

(87) PCT Pub. No.: WO2019/131119
PCT Pub. Date: Jul. 4, 2019

(65) Prior Publication Data
US 2020/0324036 A1    Oct. 15, 2020

(30) Foreign Application Priority Data

Dec. 26, 2017    (JP) .............................. JP2017-249135

(51) Int. Cl.
*A61M 1/16*    (2006.01)
(52) U.S. Cl.
CPC .......... *A61M 1/167* (2014.02); *A61M 1/1672* (2014.02)
(58) Field of Classification Search
CPC ... A61M 1/167; A61M 1/1672; A61M 1/1666
See application file for complete search history.

(56) References Cited

U.S. PATENT DOCUMENTS

| 5,437,836 A * | 8/1995 | Yamada .............. A61M 1/0001 210/257.2 |
| 2003/0168120 A1* | 9/2003 | Brehm ................ A61M 1/1666 141/313 |
| 2012/0310150 A1 | 12/2012 | Brandl et al. |

(Continued)

FOREIGN PATENT DOCUMENTS

| CN | 102921257 A | 2/2013 |
| JP | 2002537916 A | 11/2002 |

(Continued)

OTHER PUBLICATIONS

Office Action issued in CN201880083567.6 dated May 16, 2022.

*Primary Examiner* — Krishnan S Menon
(74) *Attorney, Agent, or Firm* — The Webb Law Firm (57) ABSTRACT

A dialysate solution container includes a flexible first bag body. The dialysate solution container further includes a second bag body which has a mixing region for mixing a first powdered pharmaceutical agent and water at a lower end portion of a second interior. The second bag body further has a communication pipe that places the exterior of the second bag body and the second interior in communication, and a first filter which is in communication with a first interior of the first bag body. A first end of the communication pipe is capable of being connected to a dialysis circuit, and a second end thereof is disposed within the mixing region.

20 Claims, 8 Drawing Sheets

(56) References Cited

U.S. PATENT DOCUMENTS

| | | | | |
|---|---|---|---|---|
| 2013/0004593 A1* | 1/2013 | Kloeffel | ............... | A61M 1/1668 |
| | | | | 206/525 |
| 2014/0144794 A1* | 5/2014 | Eyrard | .................. | A61J 1/1406 |
| | | | | 206/219 |
| 2017/0007541 A1* | 1/2017 | Eyrard | ................ | A61M 1/1656 |

FOREIGN PATENT DOCUMENTS

| JP | 2005512616 A | 5/2005 |
|---|---|---|
| JP | 2013514099 A | 4/2013 |
| JP | 2017509451 A | 4/2017 |

\* cited by examiner

VIEW ALONG ARROW A

DIALYSATE SOLUTION CONTAINER

CROSS-REFERENCE TO RELATED APPLICATIONS

This application is the United States national phase of International Application No. PCT/JP2018/045549 filed Dec. 11, 2018, and claims priority to Japanese Patent Application No. 2017-249135 filed Dec. 26, 2017, the disclosures of which are hereby incorporated by reference in their entirety.

BACKGROUND

The present disclosure is related to a container for a dialysate solution.

DESCRIPTION OF RELATED ART

Conventionally, there are a continuous method, in which a solution in which a pharmaceutical agent is dissolved and RO water are continuously mixed to produce a dialysate solution, and a batch method, in which a pharmaceutical agent and RO water are supplied to a container and a process to mix the pharmaceutical agent and the RO water to produce a dialysate solution, as systems for producing dialysate solutions to be employed in dialysis therapy.

In addition, there is a prepacking system, in which a pharmaceutical agent is stored in a container in advance, and RO water is supplied to the container to mix the pharmaceutical agent with the RO water to thereby produce a dialysate solution (refer to PCT Japanese Phase Publication No. 2005-512616).

However, the conventional continuous method requires a number of containers corresponding to the number of types of pharmaceutical agents to be utilized for storing solutions in which the drugs are dissolved in advance. Therefore, a comparatively large space is necessary as the containers are fixed to an apparatus, it is necessary to prepare the solutions in which the pharmaceutical agents are dissolved in advance, and also necessary to control a pump to accurately mix and dilute the solutions with RO water.

The batch method requires a number of containers corresponding to the number of types of pharmaceutical agents according to the types of pharmaceutical agents to be utilized and a container for batch processing. Therefore, a comparatively large space is necessary as the containers are fixed to an apparatus, as well as labor which is involved in the batch processing.

SUMMARY

Therefore, it is an object of the present disclosure to provide a container for a dialysate solution which is capable of reducing the amount of labor involved in producing a dialysate solution.

According to one aspect of the present disclosure, dialysate solution container comprising: a flexible first bag body, and a flexible second bag body; the second bag body comprising: a mixing region at a lower end portion of a second interior, in the mixing region a first powdered pharmaceutical agent is mixed with water; a communication pipe by means of which the exterior of the second bag body is in communication with the second interior; and a first filter in communication with a first interior of the first bag body; wherein a first end of the communication pipe is connectable to a dialysis circuit, and a second end of the communication pipe is disposed in the mixing region.

According to the present disclosure, a dialysate solution container which is capable of reducing the amount of labor involved in producing a dialysate solution can be provided.

DESCRIPTION

Hereinafter, embodiments of the present disclosure will be described in detail with reference to the attached drawings.

First Embodiment

Hereinafter, an embodiment (first embodiment) will be described in detail with reference to the drawings. Note that the same elements will be denoted by the same numbers or symbols throughout the entirety of the description of the embodiments.

Note that hereinafter, an embodiment which is related to a dialysate solution container 100, in which a first bag body 10 surrounds a second bag body 20 having a first powdered pharmaceutical agent sealed therein and a third bag body 30 having a second powdered pharmaceutical agent sealed therein will be described. However, the present disclosure is not limited to such a configuration, and a dialysate solution container need not be equipped with the third bag body 30 having the second powdered pharmaceutical agent sealed therein. Alternatively, the second bag body 20 or the third bag body 30 need not be surrounded by the first bag body 10, as long as the respective interiors thereof (a second interior and a third interior) are in direct or indirect communication with a first interior of the first bag body 10 (a second embodiment to be described later).

Figure 1:
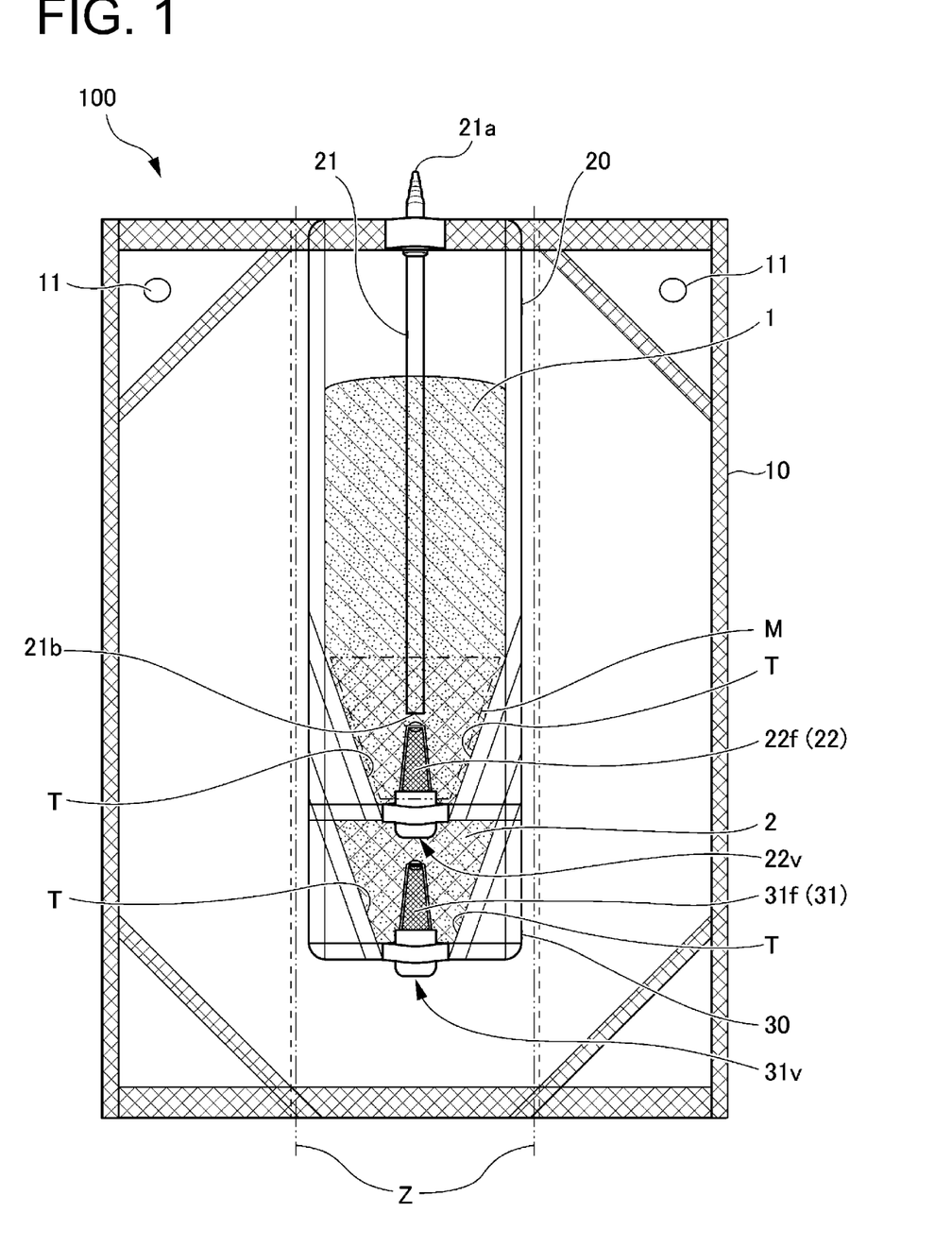
FIG. 1 is a front view of a dialysate solution container according to a first embodiment, in a state in which a first powdered pharmaceutical agent and a second powdered pharmaceutical agent are sealed therein.
Figure 2:
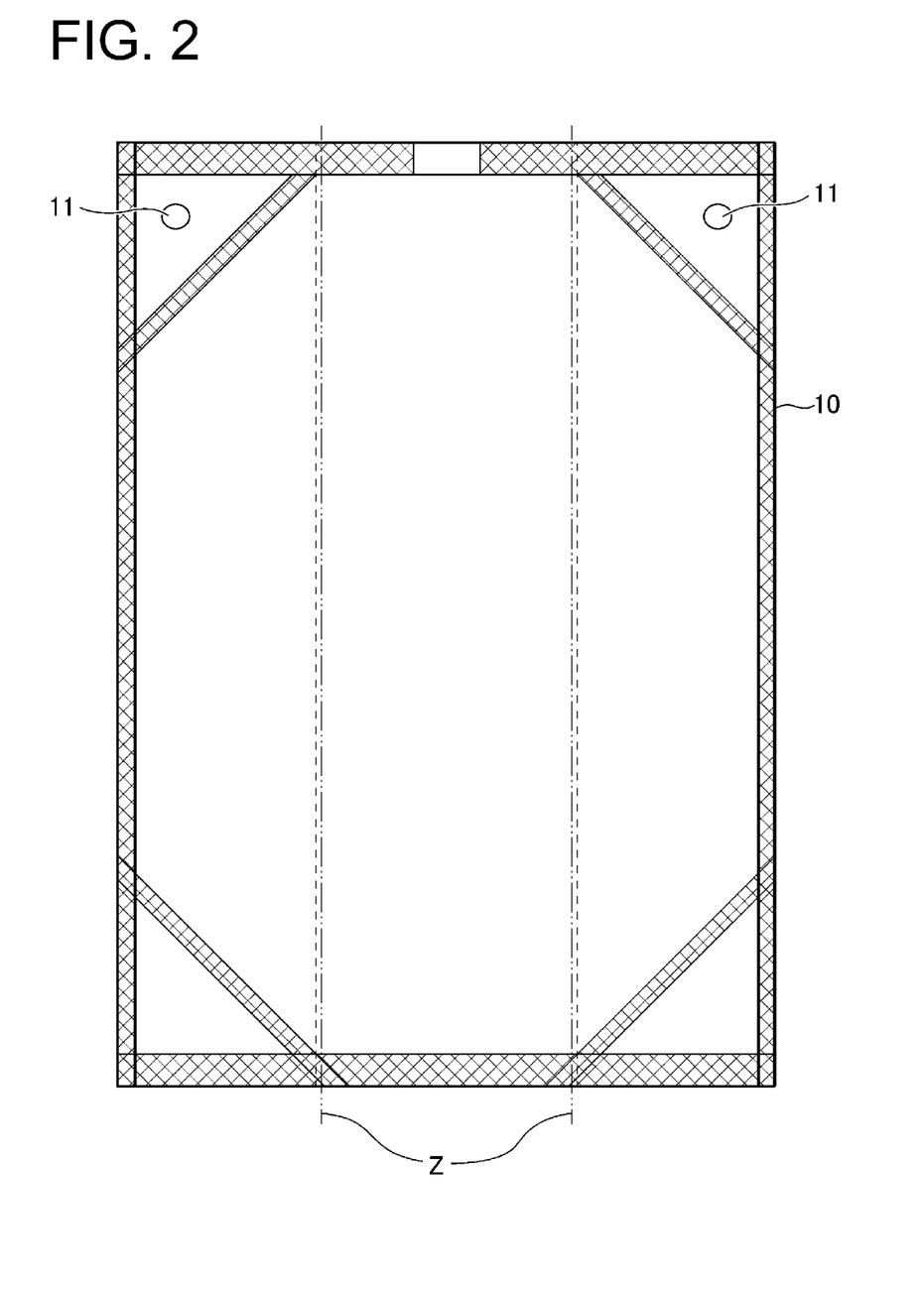
FIG. 2 is a front view of a first bag body.
Figure 3:
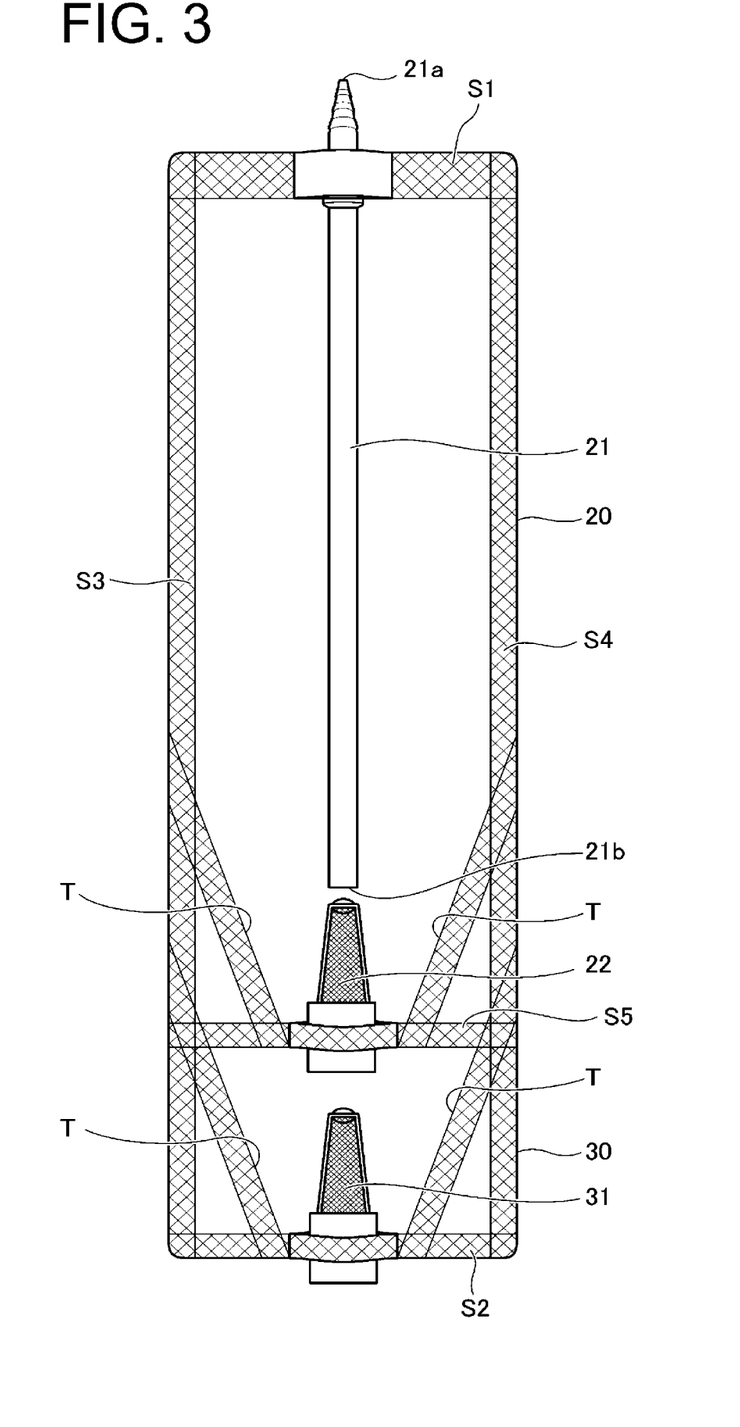
FIG. 3 is a front view of a second bag body and a third bag body.
Figure 4:
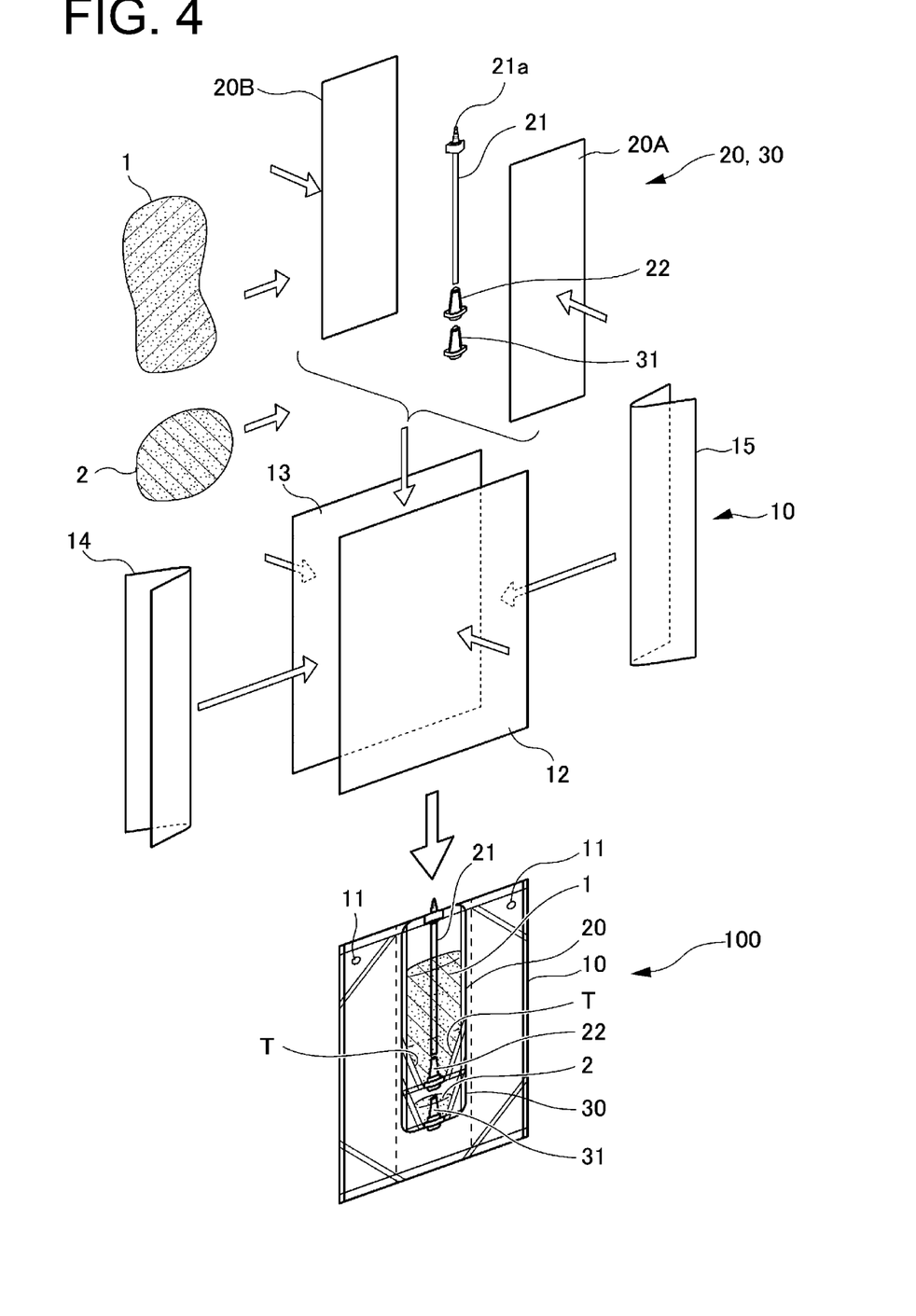
FIG. 4 is an assembly diagram of the dialysate solution container according to the first embodiment.
Figure 5:
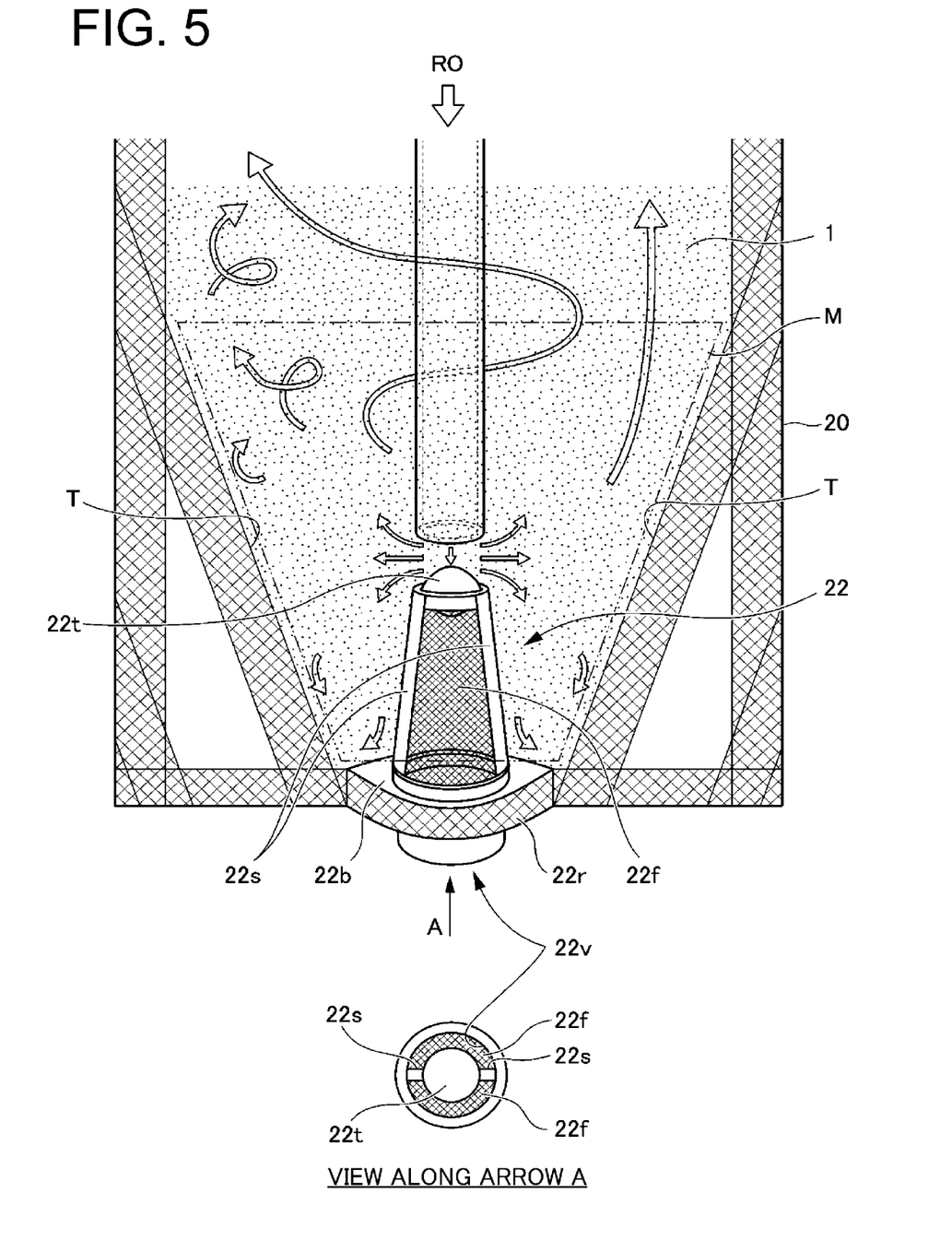
FIG. 5 is a detailed diagram or explaining the flow of water RO and the first powdered pharmaceutical agent within the second bag body.
Figure 6:
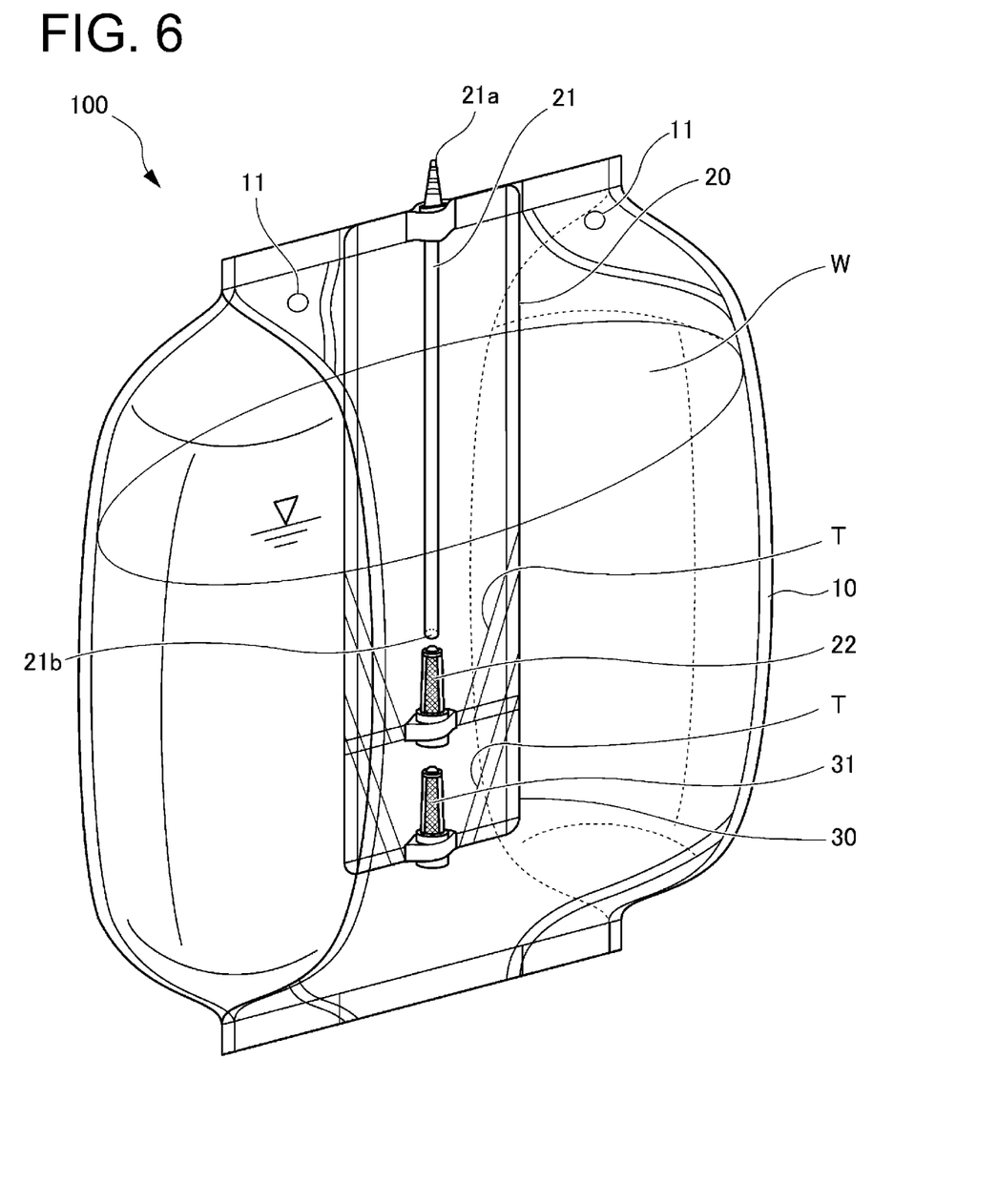
FIG. 6 is a perspective view of the dialysate solution container in a state in which a produced dialysate solution is contained therein.

FIG. 1 is a front view of the dialysate solution container 100 according to the first embodiment, in a state in which the first powdered pharmaceutical agent and the second powdered pharmaceutical agent are sealed therein. FIG. 2 is a front view of the first bag body 10. FIG. 3 is a front view of the second bag body 20 and the third bag body 30. FIG. 4 is an assembly diagram of the dialysate solution container 100 according to the first embodiment. FIG. 5 is a detailed diagram or explaining the flow of water RO and the first powdered pharmaceutical agent within the second bag body 20. FIG. 6 is a perspective view of the dialysate solution container 100 in a state in which a produced dialysate solution W is contained therein.

As illustrated in FIG. 1 and FIG. 6, the dialysate solution container 100 of the present embodiment is employed to produce the dialysate solution W. The dialysate solution W which is produced by the dialysate solution container 100 is supplied to a dialysis circuit (not illustrated) of a dialysate solution supply apparatus that includes a dialyser. The dialysate solution container 100 has a volume of approximately 15 liters, which is the amount of a dialysate solution which is generally required for an hour of dialysis treatment. Note that the dialysis circuit is provided with a switching valve which is capable of switching between injection of water RO to the dialysis solution container 100 and discharge of the dialysate solution W therefrom.

The dialysate solution container 100 is equipped with the flexible first bag body 10 and the flexible second bag body 20 which has a mixing region M at the lower end portion of the second interior (a chamber which is the housing space of the second bag body 20).

Here, the dialysate solution container 100 is disposed such that the vertical direction in FIG. 1 is the direction of gravity. For example, the dialysis solution container 100 is supported by being suspended by a suspension member (not illustrated) through support apertures which are formed in support portions 11 provided at the left and the right at the upper end portion of the first bag body 10, in a state immediately prior to the water RO being injected or in a state after the water RO has been injected. Note that when the water RO is injected, water pressure will cause the first bag body 11 to expand such that the shape thereof as a whole becomes a barrel shape (refer to FIG. 6) and stabilizes. Therefore, in such a case, the support portions 11 need not be utilized, and the bottom portion of the dialysate solution container 100 may be directly placed on a flat surface such as a floor.

The water RO is so called RO (reverse osmosis) water from which impurities have been removed by administering a reverse osmosis process, which is generally employed in dialysis treatment.

The first bag body 10 has a first interior which is capable of storing the dialysate solution W. Taking convenience during shipment and storage, as well as the fact that the first bag body 10 is freely deformable without depending on the limitations of a space in which the first bag body 10 is installed into consideration, the first bag body 10 is flexible, soft, capable of being bent, and capable of being folded. The first bag body 10 is flexible as described above. Therefore, the first bag body 10 can be folded into thirds at the positions indicated by the double dotted chain lines Z in FIG. 1 and FIG. 2, for example, to be made compact. Therefore, even if a plurality of the first bag bodies 10 are stacked, they can be transported and stored in a small space.

The first bag body 10 stores the produced dialysate solution. Therefore, the first bag body 10 has a strength and a rigidity to degrees which are capable of withstanding internal pressure exerted by the dialysate solution W. It is preferable for the first bag body 10 to be water resistant, to have chemical resistance to aqueous solutions of electrolytes such as an aqueous solution of sodium chloride or aqueous solutions of hydrogen carbonates such as an aqueous solution of sodium hydrogen carbonate, and to be transparent or translucent such that the contents can be confirmed. Polyethylene terephthalate (PET), polyethylene (PE), etc. may be employed as the material of the first bag body 10.

The first bag body 10 surrounds the second bag body 20. Thereby, the dialysate solution W that flows out from the second interior of the second bag body 20 through the first filter 22 of the second bag body 20 can be stored in the first interior of the first bag body 10.

In addition, as illustrated in FIG. 1 and FIG. 6, the first bag body 10 may surround the second bag body 20 and the third bag body 30. Thereby, a solution, in which the first powdered pharmaceutical agent 1 is dissolved, may flow out through the first filter 22 to the third interior of the third bag body 30 where the second powdered pharmaceutical agent 2 is dissolved to produce the dialysate solution W, and then the dialysate solution W may be stored in the first interior of the first bag body 10.

The second bag body 20 is employed in a state in which the first powdered pharmaceutical agent 1 is sealed therein in advance. The second bag body 20 has a communication pipe 21 that places the exterior of the second bag body 20 and the second interior in communication, and the first filter 22 which is in communication with the first bag body 10. Taking the fact that the second bag body 20 is freely deformable without depending on the limitations of a space in which the second bag body 20 is installed into consideration, the second bag body 20 is flexible, soft, capable of being bent, and capable of being folded in the same manner as the first bag body 10.

In addition, it is preferable for the second bag body 20 to be water resistant, to have chemical resistance to aqueous solutions of electrolytes such as an aqueous solution of sodium chloride or aqueous solutions of hydrogen carbonates such as an aqueous solution of sodium hydrogen carbonate, and to be transparent or translucent such that the contents can be confirmed, in the same manner as the first bag body 10. Polyethylene terephthalate (PET), polyethylene (PE), etc. may be employed as the material of the second bag body 20.

In addition, the second bag body 20 contacts the first powdered pharmaceutical agent 1 which is sealed therein. Therefore, it is preferable for the second bag body 20 to have chemical resistance to electrolytes such as sodium chloride and hydrogen carbonates such as sodium hydrogen carbonate.

A first end 21a of the communication pipe 21 is capable of being connected to the dialysis circuit (not illustrated), and a second end 21b is provided within the mixing region M (the region which is surrounded by the double dotted chain line in FIG. 1 and FIG. 5). The first end 21a of the communication pipe 21 is mounted within the second interior of the second bag body 20 in a watertight manner except for an opening for communicating with the dialysis circuit. Note that the second end 21b may have a tapered inner chamber in order to increase the flow velocity of the water RO which is caused to flow into the second interior of the second bag body 20 through the communication pipe 21.

As described above, the first powdered pharmaceutical agent 1 and the second end 21b of the communication pipe 21 are both disposed in the mixing region M at the lower end of the second interior of the second bag body 20. Therefore, the water RO that flows from the exterior into the second interior of the second bag body 20 through the communication pipe 21 is discharged into the mixing area M where the first powdered pharmaceutical agent 1 is stored by the force of gravity and acts directly on the first powdered pharmaceutical agent 1. Next, a jet flow, in which the first powdered medicine 1 is mixed, is generated in the mixing region M, and the first powdered pharmaceutical agent 1 is dissolved. Accordingly, the labor (energy) involved in producing the dialysate W can be reduced because it is not necessary to impart energy from the exterior other than fluid energy, which is generated by positioning, velocity, pressure, etc., that causes the water RO to flow through the communication pipe 21 into the second interior of the second bag body 20.

Note that in the present embodiment, the communication pipe 21 extends along the vertical direction, the first end 21a of the communication pipe 21 is disposed at the upper portion in the vertical direction, and the second end 21b is disposed at the lower portion in the vertical direction. However, the present disclosure is not limited to such a configuration. As long as the second end 21b is disposed within the mixed area M, the first end 21a may be disposed, for example, directly adjacent to the second end 21b. In the case that the first end 21a of the communication pipe 21 is disposed above the second end 21b in the vertical direction, the fluid energy of the water RO can be increased for the amount that potential energy increases.

The second bag body 20 has a single communication pipe 21. Thereby, the water RO can be injected the dialysis circuit without searching for a connection target from, because the first end 21a of the communication pipe 21 that functions as the water RO injection port is located at a single location. In addition, since the second bag body 20 has the single communication pipe 21, it connecting to and disconnecting from the dialysis circuit are facilitated. It is possible for the single communication pipe 21 to be used both for injecting the water RO and discharging the dialysate W, simply by switching the direction of flow with a switching valve which is provided in the dialysis circuit.

In addition, the first filter 22 of the second bag body 20 is disposed in the mixing region M. The first filter 22 allows a solution in which the first powdered pharmaceutical agent 1 is dissolved in the water RO to pass therethrough, but does not allow the first powdered pharmaceutical agent 1 to pass in its powder state. The first filter 22 is a mesh having openings or pore diameters smaller than the particle size of the first powdered pharmaceutical agent 1.

The second bag body 20 has a narrow portion T at the lower end portion in the second interior, which narrows the space in the second interior such that the lowermost end is adjacent to the outermost diameter portion of the first filter 22. That is, the lowermost end of the narrow portion T has substantially the same internal dimensions as the outermost diameter portion of the first filter 22. The same applies to a narrow portion T of the third bag body 30. Thereby, there are no corners at which the first powdered pharmaceutical agent 1 remains around the first filter 22, which is the lowermost end of the second interior. The flow of the water RO which is discharged from the second end 21b of the communication pipe 21 collides with the narrow portion T while entraining the first powdered pharmaceutical agent 1 while mixing the first powdered pharmaceutical agent 1 thereinto, splits into an upward flow and a downward flow, and the upward flow component increases. Therefore, in the second interior, the flow of the water RO which is discharged from the second end 21b of the communication pipe 21 does not stop, and the first powdered pharmaceutical agent 1 which is deposited in the second interior can be effectively mixed. As a result, it is possible for the first powdered pharmaceutical agent 1 to be efficiently dissolved in the water RO (refer to FIG. 5).

Note that the narrow portion T is not limited to being of a tapered shape in which linear inclined portions that narrow the second interior in the downward direction as illustrated in FIG. 5. As long as the narrow portion T is adjacent to the outermost diameter portion of 22, the narrow portion T may be inwardly convex curved portions which have shapes that face each other. As another alternative, the narrow portion T may be a combination of a taper shape and a straight shape, in which the upper portion is tapered and the lower portion has a straight shape along the direction of gravity.

As illustrated in FIG. 5, the first filter 22 is equipped with a base portion 22b which has an opening 22v in the center and a perimeter 22r which is mounted within the second bag body in a watertight manner, legs 22s that extend upward from the base 22b, a top 22t which is supported by the legs 22s, and a filter portion 22f provided between the base 22b, the legs 22s and the top 22t.

The filter portion 22f is of a curved shape as a partial cone, for example. The first filter 22 is of a substantially conical shape as a whole, and is of a three dimensional shape which is convex in the upward direction. As described above, because the first filter 22 has the top 22t, the flow of the jetted water RO collides with the top 22t and is split into the up, down, left, and right directions. Therefore, particularly in the mixing region M, it is possible for the flow of the water RO to be evenly distributed, and it is possible for the first powdered pharmaceutical agent 1 to be dissolved efficiently. In addition, because the first filter 22 has an upwardly convex three dimensional curved surface, it is possible for the area of the filter portion 22f to be as large as possible in a limited space. As a result, it is possible for the solution in which the first powdered pharmaceutical agent 1 is dissolved in the water RO to be efficiently passed through to the first interior of the first bag body 10 or the third interior of the third bag body 30. The same applies to a second filter 31.

Note that the shape of the first filter 22 is not limited to a three dimensional shape which is convex in the upward direction, and the first filter 22 may be of any shape that divides the flow of the jetted water RO into multiple directions of up, down, left, and right.

The first filter 22 and the second filter 31 may be, for example, bag shaped filters made of a synthetic fiber such as polyester or nylon, or may be bell shaped molded filters having a mesh among support columns.

The first filter 22 and the second filter 31 are not limited to such shapes, and may be equipped with a planar filter portion 22f that covers the opening 22v, for example.

It is most desirable for the communication pipe 21 to be disposed such that a nozzle opening of the second end 21b faces the top 22t. Thereby, the water RO which is jetted from the nozzle opening at the second end 21b of the communication pipe 21 can reliably collide with the top 22t, and the flow of the jetted water RO can be split into multiple directions of up, down, left, and right.

The dialysis solution container 100 may further be equipped with a flexible third bag body 30.

The third bag body 30 is employed in a state in which the second powdered pharmaceutical agent 2 is sealed therein in advance. Thereby, it is possible for the second powdered pharmaceutical agent 2, which is of a different type from the first powdered pharmaceutical agent 1 to be stored in a dry, stable state without being in contact with the first powdered pharmaceutical agent 1. In addition, it is possible for the dialysate solution W, in which different types of powdered pharmaceutical agents are dissolved, to be produced simply by injecting the water RO into the dialysate solution container 100.

Taking the fact that the third bag body 30 is freely deformable without depending on the limitations of a space in which the third bag body 30 is installed into consideration, the third bag body 30 is flexible, soft, capable of being bent, and capable of being folded in the same manner as the first bag body 10 and the second bag body 20.

In addition, it is preferable for the third bag body 30 to be water resistant, to have chemical resistance to aqueous solutions of electrolytes such as an aqueous solution of sodium chloride or aqueous solutions of hydrogen carbonates such as an aqueous solution of sodium hydrogen carbonate, and to be transparent or translucent such that the contents can be confirmed, in the same manner as the first bag body 10 and the second bag body 20. Polyethylene terephthalate (PET), polyethylene (PE), etc. may be employed as the material of the third bag body 30.

In addition, the third bag body 30 contacts the second powdered pharmaceutical agent 2 which is sealed therein. Therefore, it is preferable for the third bag body 30 to have chemical resistance to electrolytes such as sodium chloride and hydrogen carbonates such as sodium hydrogen carbonate.

The third bag body 30 is disposed such that the third interior of the third bag body 30 is in communication with the second interior of the second bag body 20 via the first filter 22 which is provided in the second bag body 20. Note that in the present embodiment, the second bag body 20 and the third bag body 30 are integrated as illustrated in FIG. 1, FIG. 3, etc. However, the present disclosure is not limited to such a configuration. An independent third bag body 30 may be disposed so as to cover and surround the first filter 22 of the second bag body 20. Thereby, the solution of the first powdered pharmaceutical agent 1 and the water RO which is prepared in the second interior of the second bag body 20 reaches the third interior of the third bag body 30 through the first filter 22, mixes with the second powdered pharmaceutical agent 2, and becomes the dialysate solution W in which the first powdered pharmaceutical agent 1 and the spa 2 are dissolved.

In addition, the third bag body 30 has the second filter 31 which is in communication with the first bag body 10. The second filter 31 allows a solution in which the second powdered pharmaceutical agent 2 is dissolved in the water RO to pass therethrough, but does not allow the second powdered pharmaceutical agent 2 to pass in its powder state. The second filter 31 is a mesh having openings or pore diameters smaller than the particle size of the second powdered pharmaceutical agent 2.

As described above, the third bag body 30 is disposed such that the third interior of the third bag body 30 is in communication with the first interior of the first bag body 10 via the second filter 31. Therefore, it is possible for the dialysate solution W in which the spa 2 is dissolved to be stored in the first bag body 10.

Next, a method for producing the dialysate solution W using the dialysate solution container 100 according to the present embodiment and the operations when producing the dialysate solution W will be described with reference to FIG. 1 and FIG. 5. Here, the operations of a method for producing the dialysate solution W in which the first powdered pharmaceutical agent 1 is sealed in the second bag body 20 in advance and the second powdered pharmaceutical agent 2 is sealed in the third bag body 30 in advance are dissolved will be described.

(1) First, as illustrated in FIG. 1, the second bag body 20 and the third bag body 30 in which the second interior and the third interior are in communication with each other via the first filter 22 and are integrated are placed within the first interior of the first bag body 10 in a watertight manner, to form a so called double bag.

(2) The first powdered pharmaceutical agent 1 is sealed in the second interior of the second bag body 20. The second powdered pharmaceutical agent 2 is sealed in the third interior of the third bag body 30.

(3) The dialysate solution container 100 is suspended and supported by a suspension member (not illustrated) utilizing the support portion 11 which is provided in the first bag body 10 to maintain an orientation in which the vertical direction in FIG. 1 becomes the vertical direction. Note that the dialysate solution container 100 is flexible, and as it becomes filled with the dialysate solution W, it will deform into a barrel shape and stabilize as illustrated in FIG. 6. Therefore, the manner in which the dialysate solution container 100 is supported is not limited to suspension as long as the orientation of the dialysate solution container can be maintained, and the dialysate solution container 100 may be directly placed on a floor or the like.

(4). The water RO is injected into the first end 21a of the communication pipe 21 toward the second interior of the second bag body 20.

(5) When the water RO is injected into the first end 21a of the communication pipe 21, the water RO which is jetted out from the second end 21b of the communication pipe 21 collides with the top 22t of the first filter 22, and the flow thereof is split so as to disperse in multiple directions in the vertical direction and the horizontal direction. Next, the water RO of which the flow has been split repeatedly collides with the narrow portion T, the first filter 22, etc., and becomes a complex flow that includes a vortex flow. This complex flow particularly mixes and dissolves the first powdered pharmaceutical agent 1 at the mixing region M. If the injection of the water RO is continued, the water RO further mixes and dissolves the first powdered pharmaceutical agent 1 at the upper portion thereof. Here, the solution in which the first powdered pharmaceutical agent 1 is dissolved passes through the filter portion 22f of the first filter 22, and flows into the third interior of the third bag body 30 via the opening 22v (refer to FIG. 1).

(6) The solution which has flowed into the third interior dissolves the second powdered pharmaceutical agent 2, passes through a filter portion 31f of the second filter 31, and flows into the first interior of the first bag body 10 via an opening 31v (refer to FIG. 6).

As described above, the dialysate solution container 100 is equipped with the second bag body 20 having the mixing region M for mixing the first powdered pharmaceutical agent 1 and the water RO at the lower end portion of the second interior, and the second end 21b of the communication pipe 21 for injecting the water RO is disposed in the mixing region M. Therefore, it is possible for the vortex flow in which the first powdered pharmaceutical agent 1 is mixed into the water RO to be generated. As a result, even if the first powdered pharmaceutical agent 1 is sodium hydrogen carbonate, etc., which are difficult to dissolve in the water RO, the dialysate solution W can be produced easily, simply by injecting the water RO from the connection tube 21. In addition, even if the dialysate solution W is that in which a plurality of different types of pharmaceutical agents are dissolved, the dialysate solution W can be produced easily, simply by injecting the water RO from the connection tube 21.

Next, a method for manufacturing the dialysate solution container 100 according to the present embodiment will be described with reference to FIG. 1 through FIG. 4. Note that here, a production method for a case in which the first powdered pharmaceutical agent 1 and the second powdered pharmaceutical agent 2 are respectively sealed in the second bag body 20 and the third bag body 30 in advance. And the second bag body 20 and the third bag body 30 are surrounded by the first bag body 10 will be described.

(1) First, the second bag body 20 and the third bag body 30 are formed.

To form the second bag body 20 and the third bag body 30, first, a substantially rectangular and sheet shaped material 20A and a similar substantially rectangular and sheet shaped back material 20B are caused to overlap as illustrated in FIG. 4.

Next, the material 20A and the back material 20B are sealed by being fused or sealed by a sealing material such as an adhesive agent at a left side S3, a right side S4, a boundary S5 between the second interior and the third interior, and at the narrow portion T as illustrated in FIG. 3 so as to be watertight. That is, the second bag body 20 and the third bag body 30 are caused to be in a state in which they are partitioned by the boundary S5 and are open at an upper side S1 and a lower side S2.

Thereafter, the second interior of the second bag body 20 is filled with the first powdered pharmaceutical agent 1, and the third interior of the third bag body 30 is filled with the second powdered pharmaceutical agent 2.

Note that the portions at which the material 20A and the back material 20B are integrated in a watertight manner by an appropriate means such as by being fused are indicated by hatching with the same pattern in FIG. 1 through FIG. 3.

(2) Next, the First Bag Body 10 is Formed.

The first bag body 10 has a substantially rectangular and sheet shaped material 12 which has a larger area than the material 20A and the material 20B that constitute the second bag body 20 and the third bag body 30, a back material 13 having the same shape as that of the material 12, a left side material 14, and a right side material 15, as illustrated in FIG. 4.

The left side material 14 and the right side material 15 are sandwiched between the material 12 and the back material 13 in a state in which the right side of the left side material 14 is folded back with the center thereof as a crease, the left side of the right side material 15 is folded back with the center thereof as a crease such that the left side material 14 and the right side material 15 are disposed at the left side and the right side, respectively, and then the material 12 and the back material 13 are caused to overlap. At this time, the second bag body 20 and the third bag body 30 which were formed in the previous step are also sandwiched between the material 12 and the back material 13 such that the first end 21a of the communication pipe 21 is exposed at the exterior of the first back body 10.

The material 12 and the left side material 14 as well as the material 12 and the right side material 15 are integrated in a watertight manner by an appropriate means such as by being fused at a left end portion and a right end portion of the first bag body 10 respectively in the state in which the material 12 and the back material are overlapped. Similarly, the back material 13 and the left side material 14 as well as the back material 13 and the right side material 15 are integrated in a watertight manner by an appropriate means such as by being fused at the left end portion and the right end portion of the first bag body 10 respectively in the state in which the material 12 and the back material are overlapped. The material 12 and the back material 13 are also integrated in a watertight manner by an appropriate means such as by being fused at an upper side portion and a lower side portion of the first bag body 10.

Further, the material 12 and the left side material 14, the material 12 and the right side material 15, as well as the back material 13 and the left side material 14, the back material 13 and the right side material 15 are integrated in a watertight manner by an appropriate means such as by being fused at each of the four corners of the first bag body 10 for reinforcement.

Note that the portions of the material 12 and the back material 13 which are integrated in a watertight manner by an appropriate means such as by being fused are indicated in FIG. 2 by hatching with the same pattern.

As described above the dialysate solution container 100 is capable of being manufactured easily from standard sheet shaped materials. In addition, the dialysate solution container 100 which is produced in this manner can be folded into thirds at the positions indicated by the double dotted chain lines Z in FIG. 1, for example, to be made into a compact shape. Therefore, even if a plurality of the first bag bodies 10 are stacked, they can be stacked in a folded state and stored or transported, which saves space and facilitates handling.

According to the dialysate solution container 100, the dialysate solution container 100 is equipped with the flexible first bag body 10, the dialysate solution container 100 is also equipped with the second bag body 20 which has the mixing region M for mixing the first powdered pharmaceutical agent 1 and the water RO at the lower end portion of the second interior, and the second bag body 20 has the communication pipe 21 that places the exterior of the second bag body 20 in communication with the second interior and the second interior and the first filter which is in communication with the first interior of the first bag body 10. The first end 21a of the communication pipe 21 is capable of being connected to the dialysis circuit, and the second end 21b is disposed in the mixing region M. Therefore, the labor (energy) involved in producing the dialysate W can be reduced because it is not necessary to impart energy from the exterior other than fluid energy, which is generated by positioning, velocity, pressure, etc., that causes the water RO to flow through the communication pipe 21 into the second interior of the second bag body 20.

Second Embodiment

Next, a dialysate solution container 100A according to a second embodiment will be described.

Figure 7:
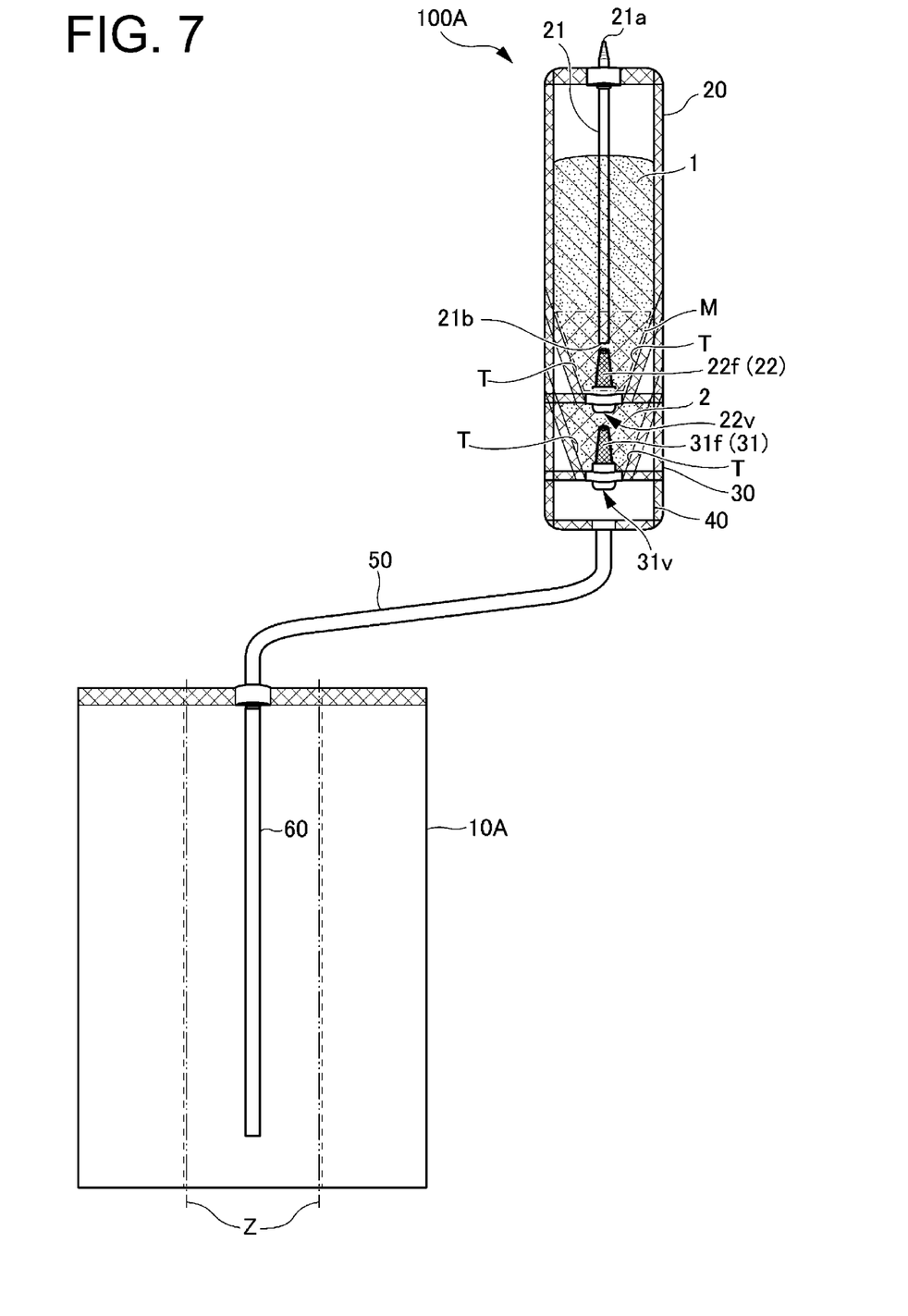
FIG. 7 is a front view of a dialysate solution container according to a second embodiment.
Figure 8:
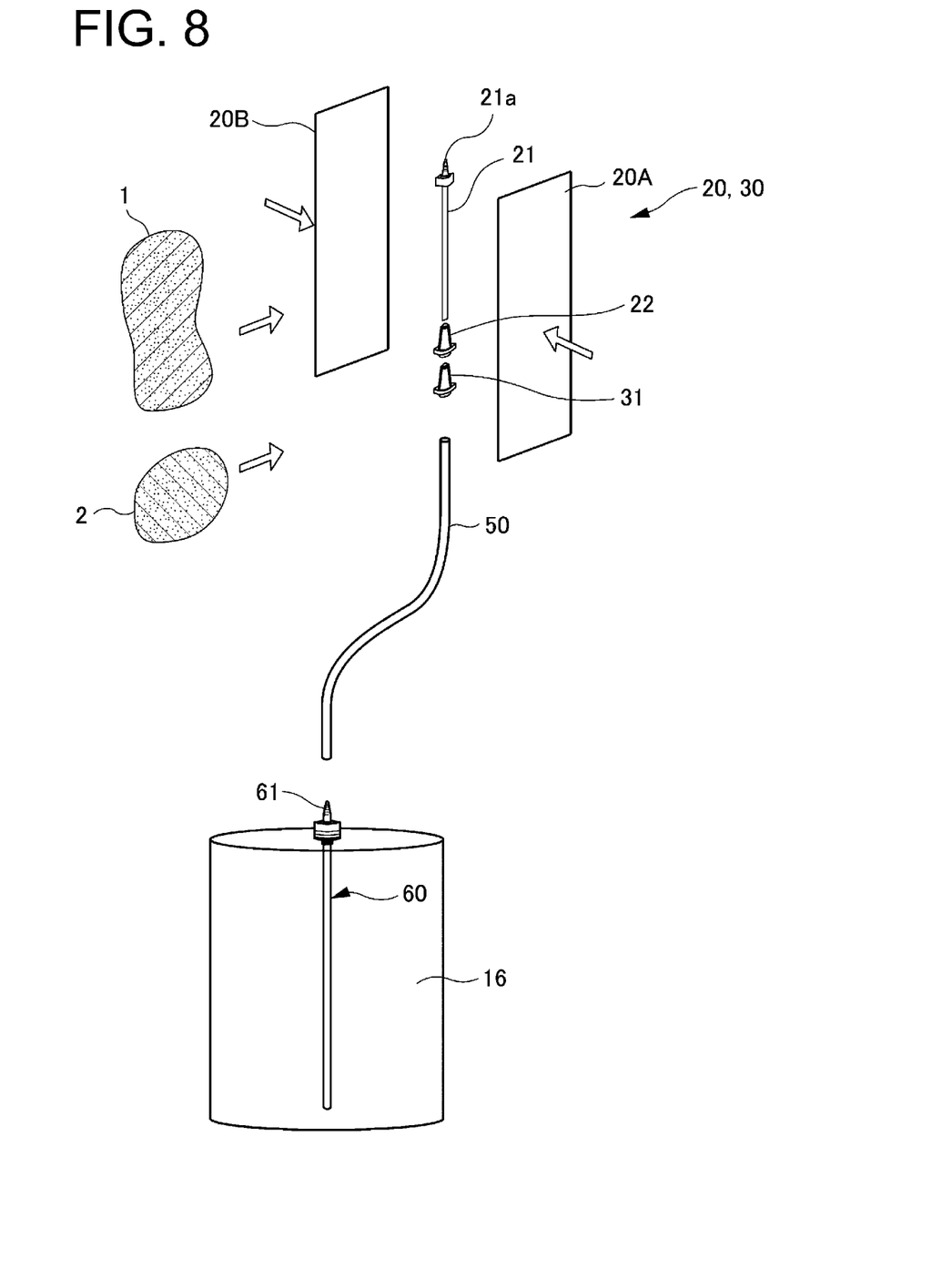
FIG. 8 is an assembly diagram of the dialysate solution container according to the second embodiment.

FIG. 7 is a front view of the dialysate solution container 100A according to the second embodiment, and FIG. 8 is an assembly diagram of the dialysate solution container 100A according to the second embodiment.

The dialysate container 100A according to the second embodiment differs from the dialysate container 100 according to the first embodiment described above mainly in the points that that the first bag body 10 is replaced with the first bag body 10A, and the second bag body 20 and the third bag body 20 are provided at the exterior of the first bag body 10A. In the following description and FIG. 7, components which are the same as the components which were described above in the first embodiment may be denoted by the same reference numerals and descriptions thereof may be omitted.

The first bag body 10A has an arbitrary volume, which is for example, about 15 liters, which is the amount of a dialysate solution which is generally required for an hour of dialysis treatment. The first bag body 10A differs from the first bag body 10 of the first embodiment described above in that the support portion 11 is omitted. However, the first bag body 10A may have the support portion 11.

Note that a single first bag body 10A may be formed by the substantially rectangular and sheet shaped front material 12, the similar backing material 13, the left side material 14, and the right side material 15 in a manner similar to the first bag body 10 of the first embodiment described above (refer to FIG. 4). However, it is preferable for the first bag body 10A to be formed by a single bag shaped material (refer to the material 16 illustrated in FIG. 8). In this case, simplification of the first bag body 10A (reduction of manufacturing costs) can be achieved. The upper side portion of the first bag body 10A is integrated (sealed) in a watertight manner by an appropriate means such as by being fused except for a portion that a second communication pipe 60 passes through. Note that in FIG. 7, the portions which are integrated in a watertight manner by appropriate means such as by being fused are indicated by hatching with the same pattern as in FIG. 2.

Because the first bag body 10A is flexible in a manner similar to that of the first bag body 10 of the first embodiment described above, it can be folded in any manner. For example, the first bag body 10A can be folded back and folded at the positions indicated by the double dotted chain lines Z in FIG. 7 and be made into a compact shape. Therefore, the dialysis solution container 100A exhibits superior portability, is not bulky when transported or stored, and is capable of saving space.

The second bag body 20 and the third bag body 30 of the present embodiment have the same configurations as those of the first embodiment described above, except in the point that the second bag body 20 and the third bag body 30 are provided at the exterior of the first bag body 10A.

In addition, a buffer chamber 40 is provided below the third bag 30 in the present embodiment. The buffer chamber 40 has a function of temporarily storing a solution (water RO in which the first powdered pharmaceutical agent 1 and the second powdered pharmaceutical agent 2 are dissolved) that flows downward from the interior of the third bag body 30 via the second filter 31. The buffer chamber 40 is provided so as to seal the opening 31v of the second filter 31. Accordingly, the solution that flows downward through the second filter 31 is prevented from leaking out of the dialysate solution container 100A.

The buffer chamber 40 may be formed using a front material and a back material (not shown) similar to the front material 20A and the back material 20B (refer to FIG. 8) for forming the second bag body 20 and the third bag body 30. The buffer chamber 40 may be formed in the same manner that the third bag body 30 is formed. However, because the buffer chamber 40 does not need to have the narrow portion T, it can be formed more easily. Note that in a modification, a narrow portion T may be formed in the buffer chamber 40 as well.

Note that in the example which is illustrated in FIG. 7, the buffer chamber 40 is a bag having the same width as the second bag body 20 and the third bag body 30. However, the buffer chamber 40 may be a bag having a smaller width than the second bag body 20 and the third bag body 30, and the shape, etc. may be arbitrary.

Note that the opening 31v of the second filter 31 may be covered with a diaphragm membrane (not illustrated) for preventing the second powdered pharmaceutical agent 2 from falling (moving to the buffer chamber 40) in a state where the water RO is not introduced. In this case, the diaphragm membrane has a property of being torn by the pressure when the water RO is introduced. Note that such a diaphragm membrane may be provided for the opening 22v of the first filter 22.

An upper end of a first connection pipe 50 is connected to the lower portion of the buffer chamber 40. The lower side portion of the buffer chamber 40 is integrated (sealed) in a watertight manner by an appropriate means such as by being fused except for a location at which the first connection pipe 50 passes through. Note that a joint portion which is capable of connecting with the upper end of the first connection pipe 50 may be integrated with the lower portion of the buffer chamber 40 instead of the upper end of the first connection pipe 50.

The upper end of the first connection pipe 50 is connected to the lower portion of the buffer chamber 40 as described above. At the same time, the lower end of the first connection pipe 50 is connected to an upper end 61 of a second connection pipe 60. Note that the upper end 61 of the second connection pipe 60 may function as a joint portion in the same manner as the first end 21a of the communicating pipe 21. In this case, it is possible for the first connection pipe 50 and the second connection pipe 60 to be connected by fitting the lower end of the first connection pipe 50 into the upper end 61 of the second connection pipe 60.

It is preferable for the first connection pipe 50 to be flexible, and the first connection pipe 50 is formed by a material such as rubber, a resin that imparts flexibility (polyvinyl chloride and silicone, for example), etc. In this case, the dialysate solution container 100A in a state in which the second bag body 20 and the third bag body 30 are connected to the first bag body 10A is not bulky, and flexibility, etc. will be favorable. In addition, the second connection pipe 60 may be formed by an inflexible material, or may be formed by a material such as rubber, a resin that imparts flexibility.

Note that in a modification, the first connection pipe 50 and the second connection pipe 60 may be realized by a single pipe channel member. Alternatively, the first connection pipe 50 and the second connection pipe 60 may be realized by three or more pipe channel members. In addition, the location at which the first connection pipe 50 and the second connection pipe 60 are connected is arbitrary, and is not limited to the upper portion of the first bag body 10A as described above. For example, the upper end 61 of the second connection pipe 60 may extend to the exterior of the first bag body 10A, and the lower end of the first connection pipe may be connected thereto at the exterior of the first bag body 10A.

In addition, the connection between the first connection pipe 50 and the second connection pipe 60 may be that of a non removable format (press fitting, for example), or may be that of a removable format.

As described above, the upper end 61 of the second connection pipe 60 is connected to the first connection pipe 50, and the lower end opens into the first interior of the first bag body 10A. It is preferable for the lower end of the second connection pipe 60 to be located in the vicinity of the bottom portion of the first interior of the first bag body 10A. In this case, it is possible for substantially all of the dialysate solution W (the produced dialysate W) which is formed in the first interior of the first bag body 10A to be discharged to the dialysis circuit at the exterior of the first bag body 10A via the transferred to the second connection pipe 60, the first connection pipe 50, the third bag body 30, the second bag 20, and the communication pipe 21. That is, the utilization efficiency of the produced dialysate W can be improved.

According to the dialysate solution container 100A according to the present embodiment as described above, it is not necessary for the second bag body 20 and the third bag body 30 to be housed within the first bag body 10. Therefore, it is possible for the first bag body 10A to be easily manufactured from a bag shaped material. As a result, it is possible to achieve a reduction in manufacturing cost.

Note that in the dialysate solution container 100A described above, the buffer chamber 40 is formed of a flexible material (the material that forms the second bag body 20 and the third bag body 30). However, the present disclosure is not limited to such a configuration. For example, the buffer chamber 40 may be formed of a resin member that can be attached to the lower portion of the second filter 31 in a watertight manner. Alternatively, the buffer chamber 40 may be formed integrally with the second filter 31.

Note that in the present embodiment, the first connection pipe 50 and the second connection pipe 60 cooperate to form an example of a connection pipe having a first end that extends into the first interior of the first bag body 10A and a second end which is in communication with the first filter 22. Note that in this case, the second end of the first connection pipe 50 is in communication with the first filter 22 via the third bag 30.

Next, a method for producing the dialysate solution W using the dialysate solution container 100A according to the present embodiment and the operations when producing the dialysate solution W will be described.

(1) First, the dialysate solution container 100A, in which the first powdered pharmaceutical agent 1 is sealed in the second interior of the second bag body 20 in advance and the second powdered pharmaceutical agent 2 is sealed in the third interior of the third bag body 30 in advance, is in a predetermined orientation in a manner similar to the case of the dialysate solution container 100 described above. The second bag body 20 and the third bag body 30 are set in an upright orientation, and the first bag body 10A is set at a position below the second bag body 20 and the third bag body 30.

(2) Next, the water RO is injected into the first end 21a of the communication pipe 21 toward the second interior of the second bag body 20.

(3) When the water RO is injected into the first end 21a of the communication pipe 21, the water RO which is jetted out from the second end 21b of the communication pipe 21 collides with the top 22t of the first filter 22, and the flow thereof is split so as to disperse in multiple directions in the vertical direction and the horizontal direction in a manner similar to the case of the dialysate solution container 100 described above. Next, the water RO of which the flow has been split repeatedly collides with the narrow portion T, the first filter 22, etc., and becomes a complex flow that includes a vortex flow. This complex flow mixes and dissolves the first powdered pharmaceutical agent 1 particularly in the mixing region M. If the injection of the water RO is continued, the water RO further mixes and dissolves the first powdered pharmaceutical agent 1 at the upper portion. Here, the solution in which the first powdered pharmaceutical agent 1 is dissolved passes through the filter portion 22f of the first filter 22, and flows into the third interior of the third bag body 30 via the opening 22v (4) The solution which has flowed into the third interior dissolves the second powdered pharmaceutical agent 2, passes through a filter portion 31f of the second filter 31, and flows into the first interior of the first bag body 10 via the first connection pipe 50 and the second connection pipe 60 (refer to FIG. 7), and is stored as the dialysate solution W.

As described above, the dialysate solution container 100A is equipped with the second bag body 20 having the mixing region M for mixing the first powdered pharmaceutical agent 1 and the water RO at the lower end portion of the second interior, and the second end 21b of the communication pipe 21 for injecting the water RO is disposed in the mixing region M. Therefore, it is possible for the vortex flow in which the first powdered pharmaceutical agent 1 is mixed into the water RO to be generated. As a result, even if the first powdered pharmaceutical agent 1 is sodium hydrogen carbonate, etc., which are difficult to dissolve in the water RO, the dialysate solution W can be produced easily, simply by injecting the water RO from the connection tube 21. In addition, even if the dialysate solution W is that in which a plurality of different types of pharmaceutical agents are dissolved, the dialysate solution W can be produced easily, simply by injecting the water RO from the connection tube 21.

Note that thereafter, it is possible to utilize the dialysate solution W (the produced dialysate solution W) which is formed in the first interior of the first bag body 10, by switching the direction of flow with a switching valve which is provided in the dialysis circuit. In this case, the dialysate solution W within the first interior of the first bag body 10A is discharged to the dialysis circuit at the exterior of the first bag body 10A via the second connection pipe 60, the first connection pipe 50, the third bag body 30, the second bag body 20, and the communication pipe 21. Note that in a modification, the first bag body 10A may be separated from the second bag body 20 and the third bag body 30 after the dialysate solution W is formed in the first interior of the first bag body 10A. That is, the second connection pipe 60 and the first connection pipe 50 may be in a disconnected state. In this case, it is possible for the dialysate solution W within the first interior of the first bag body 10A to be utilized by the dialysis circuit being connected to the upper end 61 of the second connection pipe 60 that extends from the first bag body 10A.

A method for manufacturing the dialysate solution container 100A according to the present embodiment may be as follows, for example.

(1) First, the second bag body 20 and the third bag body 30 are formed in the same manner as that in the case of the first embodiment described above.

Next, the second interior of the second bag body 20 is filled with the first powdered pharmaceutical agent 1, and the third interior of the third bag body 30 is filled with the second powdered pharmaceutical agent 2 in the same manner as that in the case of the first embodiment described above.

Thereafter, the buffer chamber 40 is formed by being fused, etc., and the second bag body 20 and the third bag body 30 are integrated with the communication pipe 21, the first filter 22, and the second filter 31. Note that the first filter 22 may be integrated prior to filling the second interior of the second bag body 20 with the first powdered pharmaceutical agent 1.

(2) Next, the first bag body 10A which is equipped with the second connection pipe 60 is formed. Note that in a modification, the first bag body 10A may be formed prior to the second bag body 20 and the third bag body 30 being formed.

Specifically, the first bag body 10A may be formed by placing the second connection pipe 60 in the bag shaped material 16 having a volume of approximately 15 liters, and by sealing the upper side portion of the material 16 by fusing, etc. At this time, the upper end 61 of the second connection pipe 60 is exposed at the exterior of the first bag body 10A. It is possible to form the first bag body 10A which is equipped with the second connection pipe 60 in this manner.

Note that in the present embodiment, it is possible to form the first bag body 10A with the bag shaped material 16, and therefore the necessity of fusing, etc. for reinforcement is low. Accordingly, in the case that fusing, etc. for reinforcement is omitted, a further reduction in manufacturing cost for the first bag body 10A can be achieved. However, fusing, etc. for reinforcement may be executed as necessary in the present embodiment as well.

As described above, it is possible to easily manufacture the dialysate solution container 100A from standard sheet shaped materials, a bag shaped material, etc. In addition, in the case of the present embodiment, unlike the case of the above-described first embodiment, the second bag body 20 and the third bag body 30 are provided at the exterior of the first bag body 10A, and therefore it is possible for the bag bodies to be manufactured independently. Accordingly, it is possible for the dialysate solution container 100A to be manufactured easily, and manufacturing cost can be reduced. In addition, the dialysate solution container 100A which is produced in this manner can be folded into thirds at the positions indicated by the double dotted chain lines Z in FIG. 7, for example, to be made into a compact shape. Therefore, even if a plurality of the first bag bodies 10 are stacked, they can be stacked in a folded state and stored or transported, which saves space and facilitates handling.

Embodiments of the present disclosure have been described above. However, the present disclosure is not limited to any specific embodiment. Various changes and modifications are possible within the scope which is recited in the claims. In addition, the entirety or a plurality of the constituent elements of the embodiments described above may be combined.

For example, in the embodiments described above, the flexible second bag body 20 and the flexible third bag body 30 are utilized. However, the present disclosure is not limited to such a configuration. For example, the second bag body 20 and/or the third bag body 30 may be partially or entirely inflexible. For example, the second bag body 20 and the third bag body 30 may be formed by resin. In this case, in the second bag body 20, only the portion that forms the mixed region M may be formed by resin, and the other portions may be formed by a flexible material. In this case, the portion which is formed by the resin and the portions which are formed by the flexible material may be coupled by being fused, etc.

The invention claimed is:
1. A dialysate solution container comprising:
a flexible first bag body, and
a flexible second bag body;
the second bag body comprising:
    a first powdered pharmaceutical agent sealed in a second interior of the second bag body;
    a communication pipe through which an exterior of the second bag body is in communication with the second interior;
    a mixing region at a lower end portion of the second interior for mixing the first powdered pharmaceutical agent with water injected through the communication pipe from the exterior of the second bag body; and
    a first filter, disposed at the mixing region, through which the second interior is in communication with a first interior of the first bag body,
    wherein a first end of the communication pipe is connectable to a dialysis circuit, and a second end of the communication pipe is disposed in the mixing region.
2. A dialysate solution container comprising:
a flexible first bag body, and
a second bag body, at least a part of which is formed by an inflexible material;
the second bag body comprising:
    a first powdered pharmaceutical agent sealed in a second interior of the second bag body;
    a communication pipe through which an exterior of the second bag body is in communication with the second interior;
    a mixing region at a lower end portion of the second interior for mixing the first powdered pharmaceutical agent with water injected through the communication pipe from the exterior of the second bag body; and
    a first filter, disposed at the mixing region, through which the second interior is in communication with a first interior of the first bag body,
    wherein a first end of the communication pipe is connectable to a dialysis circuit, and a second end of the communication pipe is disposed in the mixing region.
3. The dialysate solution container as defined in claim 1, wherein:
the communication pipe included in the second bag body is a single communication pipe included in the dialysate solution container though which water is capable of being injected into the dialysate solution container.
4. The dialysate solution container as defined in claim 1, wherein:
the second bag body further comprises, at the lower end portion of the second interior, a narrow portion that narrows a space within the second interior such that a lowermost end of the narrow portion is adjacent a maximum outer diameter portion of the first filter.
5. The dialysate solution container as defined in claim 1, wherein:
the communication pipe is disposed such that a nozzle opening of the second end thereof faces the first filter.
6. The dialysate solution container as defined claim 1, wherein:
the first filter comprises a top and a three dimensional curved surface which is convex in an upward direction.
7. The dialysate solution container as defined in claim 1, further comprising:
a flexible third bag body including a second powdered pharmaceutical agent;
the third bag body having a second filter which is in communication with the first bag body, and
the third bag body being disposed such that a third interior of the third bag body is in communication with the second interior of the second bag body through the first filter, and the third interior of the third bag body is in communication with the first interior of the first bag body through the second filter.
8. The dialysate solution container as defined in claim 7, wherein:
the first bag body surrounds the second bag body and the third bag body.
9. The dialysate solution container as defined in claim 1, wherein:
the first bag body surrounds the second bag body.
10. The dialysate solution container as defined in claim 1, wherein:
the second bag body is provided at an exterior of the first bag body; and
the dialysate solution container further comprises a connection pipe having a first end within the first interior of the first bag body and a second end which is in communication with the first filter.

11. The dialysate solution container as defined in claim 2, wherein:
the communication pipe included in the second bag body is a single communication pipe included in the dialysate solution container though which water is capable of being injected into the dialysate solution container.

12. The dialysate solution container as defined in claim 2, wherein:
the second bag body further comprises, at the lower end portion of the second interior, a narrow portion that narrows a space within the second interior such that a lowermost end of the narrow portion is adjacent a maximum outer diameter portion of the first filter.

13. The dialysate solution container as defined in claim 2, wherein:
the communication pipe is disposed such that a nozzle opening of the second end thereof faces the first filter.

14. The dialysate solution container as defined in claim 2, wherein:
the first filter comprises a top and a three dimensional curved surface which is convex in an upward direction.

15. The dialysate solution container as defined in claim 2, further comprising:
a flexible third bag body including a second powdered pharmaceutical agent;
the third bag body having a second filter which is in communication with the first bag body, and
the third bag body being disposed such that a third interior of the third bag body is in communication with the second interior of the second bag body through the first filter, and the third interior of the third bag body is in communication with the first interior of the first bag body through the second filter.

16. The dialysate solution container as defined in claim 15, wherein:
the first bag body surrounds the second bag body and the third bag body.

17. The dialysate solution container as defined in claim 2, wherein:
the first bag body surrounds the second bag body.

18. The dialysate solution container as defined in claim 2, wherein:
the second bag body is provided at an exterior of the first bag body; and
the dialysate solution container further comprises a connection pipe having a first end within the first interior of the first bag body and a second end which is in communication with the first filter.

19. The dialysate solution container as defined in claim 1, wherein:
the first bag body and the second bag body are configured such that solution in which the first powdered pharmaceutical agent is dissolved in the water at the mixing region of the second bag body is introduced into the first interior of the first bag body after passing through the first filter.

20. The dialysate solution container as defined in claim 2, wherein:
the first bag body and the second bag body are configured such that solution in which the first powdered pharmaceutical agent is dissolved in the water at the mixing region of the second bag body is introduced into the first interior of the first bag body after passing through the first filter.

* * * * *

UNITED STATES PATENT AND TRADEMARK OFFICE
CERTIFICATE OF CORRECTION

| | | |
|---|---|---|
| PATENT NO. | : 11,446,418 B2 | Page 1 of 1 |
| APPLICATION NO. | : 16/957193 | |
| DATED | : September 20, 2022 | |
| INVENTOR(S) | : Hiroshi Nimura et al. | |

It is certified that error appears in the above-identified patent and that said Letters Patent is hereby corrected as shown below:

In the Claims

Column 16, Line 25, Claim 3, delete "though" and insert -- through --

Column 16, Line 39, Claim 6, after "defined" insert -- in --

Column 17, Line 7, Claim 11, delete "though" and insert -- through --

Signed and Sealed this
Fifteenth Day of November, 2022

Katherine Kelly Vidal
*Director of the United States Patent and Trademark Office*